(12) United States Patent
Huijbregts et al.

(10) Patent No.: US 6,568,251 B1
(45) Date of Patent: May 27, 2003

(54) CORROSION PROBE

(75) Inventors: Walterus M. M. Huijbregts, Renkum (NL); Andreas J. M. Primus, Zevenaar (NL)

(73) Assignee: N.V. Kema, Arnhem (NL)

( * ) Notice: Subject to any disclaimer, the term of this patent is extended or adjusted under 35 U.S.C. 154(b) by 0 days.

(21) Appl. No.: 09/700,913

(22) PCT Filed: May 19, 1999

(86) PCT No.: PCT/NL99/00308

§ 371 (c)(1),
(2), (4) Date: Mar. 5, 2001

(87) PCT Pub. No.: WO99/61889

PCT Pub. Date: Dec. 2, 1999

(30) Foreign Application Priority Data

May 22, 1998 (EP) .............................................. 98201722

(51) Int. Cl.⁷ ............................................... G01N 17/00
(52) U.S. Cl. ............................................................. 73/86
(58) Field of Search ................................................ 73/86

(56) References Cited

U.S. PATENT DOCUMENTS

| | | | |
|---|---|---|---|
| 3,948,744 A | * 4/1976 | Cushing | .......................... 73/86 |
| 3,996,124 A | * 12/1976 | Eaton et al. | ..................... 73/86 |
| 4,097,341 A | 6/1978 | Schell et al. | |
| 4,563,427 A | 1/1986 | Weiss et al. | |
| 4,631,961 A | 12/1986 | Yohe et al. | |
| 4,945,758 A | * 8/1990 | Carpenter | ....................... 73/86 |

* cited by examiner

*Primary Examiner*—Robert Raevis
(74) *Attorney, Agent, or Firm*—Banner & Witcoff, Ltd.

(57) ABSTRACT

The invention relates to a device and a method for determining the quality of the corrosion on the inside of a wall manufactured from non-corrosion-resistant material of a space in which corrosive conditions prevail, wherein at least one part of the wall is removable from the wall without destructive operations and is available after removal for examination outside the space. This measure has the advantage that an element to be removed without destructive operations can be removed easily and can be replaced. Although in the first instance a screw is envisaged, other embodiments are in no way precluded, such as a pin or a prop onto which another fixation device is arranged, for instance a bayonet fitting.

11 Claims, 2 Drawing Sheets

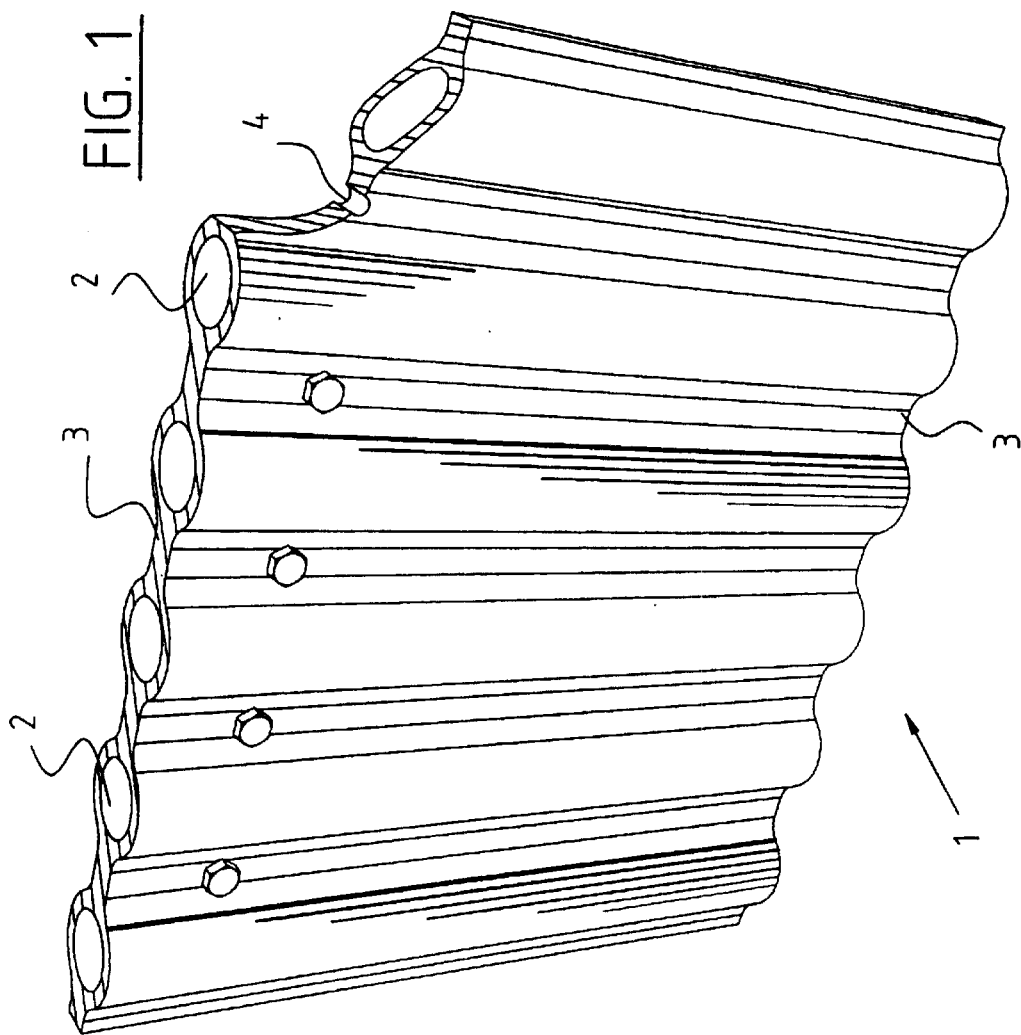
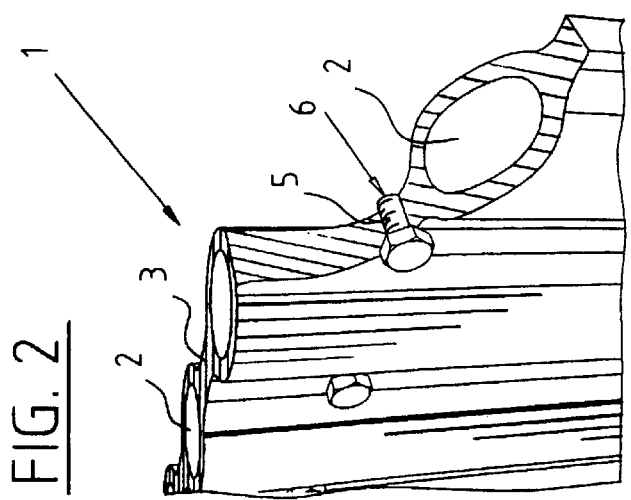

CORROSION PROBE

FIELD OF THE INVENTION

The present invention relates to a device and a method for determining the quality of the corrosion on the inside of a wall manufactured from non-corrosion-resistant material of a space in which corrosive conditions prevail.

BACKGROUND OF THE INVENTION

Such a situation occurs for instance in steam boilers which are adapted to feed for instance the steam turbines of an electric power station, as well as in other types of device such as waste incinerators, boilers provided with fire tubes and the like. In order to be able to estimate the remaining life of the wall of such an installation it is of great importance to have information concerning the thickness and other qualities of the usually inaccessible space in which such corrosive conditions prevail. Particularly in the case of an electric power station this access is especially difficult since, in order to reach the relevant side of the wall, the unit in question of the electric power station has to be shut down. This causes great economic loss.

There also usually exists a need, for instance in the case of irregularities in the process, for knowledge relating to the quality of such an oxide layer.

According to the generally known prior art, a part of the wall of the space is removed and replaced by a corresponding part, whereafter the removed wall part can be examined. This has the drawback that on the one hand the unit has to be shut down and on the other removal and re-placing of a wall part entails high cost, caused on the one hand by the length of time for which the installation must be shut down and on the other by the necessary tests enabling the quality of the welds to be determined after placing of the replacement wall part.

BRIEF DESCRIPTION OF THE INVENTION

The object of the present invention is to provide such a device and method, wherein the above stated drawbacks are avoided.

This objective is achieved in that at least one part of the wall is removable from the wall without destructive operations and is available after removal for examination outside the space.

This measure has the advantage that an element to be removed without destructive operations can be removed easily and can be replaced.

Although in the first instance a screw is envisaged, other embodiments are in no way precluded, such as a pin or a plug onto which another fixation device is arranged, for instance a bayonet fitting.

However, in the case of a water tube boiler where the walls are formed at least partially by water tubes, it is important that the heat transfer process taking place in the tubes, and thus the flow of liquid or gas through the tubes, may not be interrupted. It is therefore prudent to make such an element as small as possible. The removable wall part is then preferably formed by a bolt screwed into an opening arranged in the wall and provided with screw thread.

It is then also important that the opening is arranged in the strip between two water tubes.

In order to achieve that the corrosion occurring on the bolt has the same quality as the corrosion occurring on the other wall parts, it is important that the bolt be manufactured from the same material as the wall. This reproducibility is improved when the bolt is screwed into the opening up to a position in which the end of the screw thread of the bolt lies flush with the inner side of the wall.

In order to obtain a good resemblance between the oxide development on the actual wall and the bolt, it is important that the temperature of the bolt is substantially equal to that of the wall. The strips between the water tubes of the water tube boiler will have a slightly higher temperature than the tube walls because the tube walls are anyway cooled by the water flowing through the tubes, so that there is no case in which less oxidation occurs on the bolt surface.

To be able to make a comparison between a non-affected part of the exposed surface and an indeed affected part thereof, a part of the surface exposed to the core of the space concerned is covered by a layer of a precious metal, like gold or platina.

So as to prevent wear of the screw thread in the case of repeated screwing in and out of the bolts, the opening is preferably provided with a helicoil.

It is further noted that due to the simplicity of the present invention it becomes possible to repeatedly carry out an examination into the situation of the oxide layer, since the difficulty involved and the accompanying interruption of the operating process is extremely small. During the examination the removed part is preferably sawn through in the direction transversely of the plane of the wall, whereafter it can be inspected visually or microscopically. It will be apparent that this inspection becomes clearer when the sawn surface is polished. The polished surface is photographed in order to record the results of the examination and to enable comparison with corrosion in other situations, for instance at other locations in the same boiler, with other boilers in similar conditions, with other fuels, with the corrosion situation at an earlier or later stage. It is then possible for the photographic image of the polished surface to be converted to digital form and quantified. This provides the option of electronic processing of the results and of determining, for instance by planimetry, a rough estimate of the thickness and quality, such as porosity and sulphide content, of the oxide layer.

BRIEF DESCRIPTION OF THE DRAWINGS

The present invention will be elucidated hereinbelow with reference to the annexed figures, in which:

FIG. 1 shows a partly broken away perspective view of a tube wall of a water tube boiler in which probes according to the present invention are applied;

FIG. 2 shows a sectional view of a part of a tube wall in which is arranged a probe according to the present invention.

DETAILED DESCRIPTION OF THE INVENTION

Figure 3:
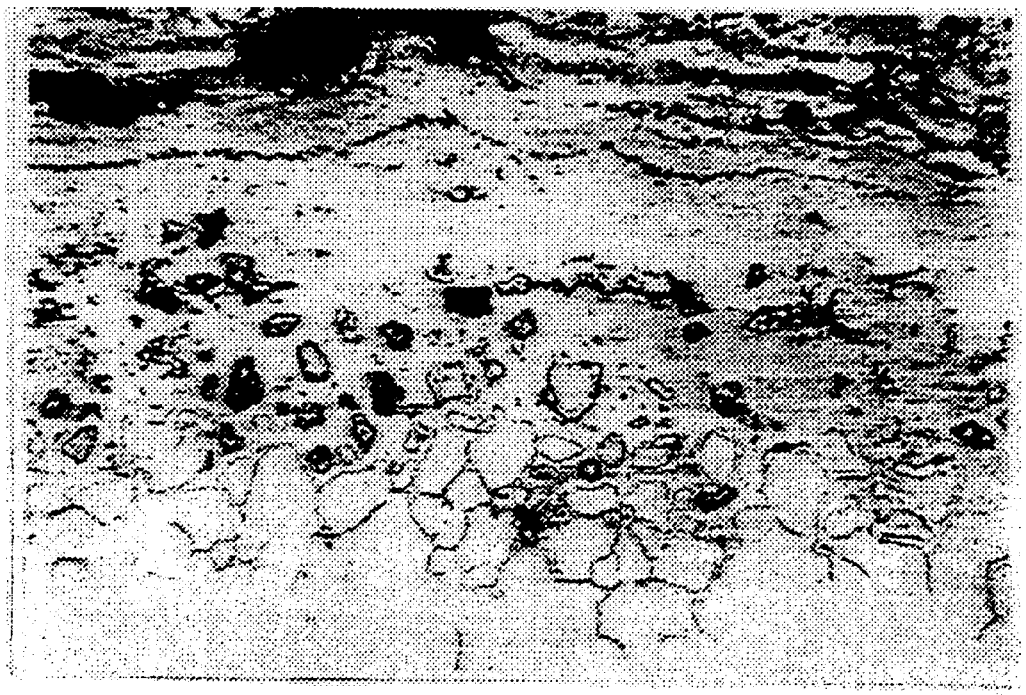
FIG. 3 shows an enlarged photo of a probe according to the invention in which the oxide layer is clearly visible.

Shown in FIG. 1 is a tube wall 1 which forms part of a water tube boiler of for instance an electric power plant. Tube wall 1 is formed by tubes 2 in which flows water or steam which is heated by the combustion process in the water tube boiler. FIG. 1 shows the inner side of the wall in question where the oxidation process occurs. Tubes 2 are mutually connected by strips 3 which have been created by welding together tubes 2.

As can be seen, a hole 4 is drilled in a number of the strips 3, into which hole is placed a bolt 5. Bolt 5 is preferably manufactured from the same material in which the tube wall is manufactured. Bolt 5 is screwed into hole 4 to a depth such that the end of the shank 6 of the bolt lies flush with the level of the inner surface of tube wall 1.

When an inner side of such a tube wall must be examined for oxidation, for instance as a consequence of periodic inspection or as a result of irregularities occurring inside the boiler, bolt 5 is loosened, replaced by a similar bolt, whereafter the end surface 6 of the bolt can be examined. A normal visual inspection is of course possible here first of all, while it is advantageous to saw through such a bolt in the length so that a cross-section of the oxide layer is obtained.

The presence of the protecting layer in the form of a layer of a precious metal allows a comparison between an affected surface and a non-affected surface.

This can in turn be examined, possibly after polishing thereof, whereafter visual inspection or microscopic examination can once again take place. Such cross-sections are herein photographed. FIG. 3 shows an example thereof.

Finally, it is possible to scan such a photo and put it in digital form, whereafter the thus obtained image can be subjected to electronic processing methods, for instance quantifying methods.

The simplicity of this inspection method enables such an inspection to be repeated periodically with relatively great frequency, so that changing conditions can be taken into account, for instance a change in fuel, different setting of burners and so on. It is moreover possible, as shown in FIG. 1, to arrange such probes at different locations lying close to one another; reproducibility of the process is hereby increased, while it is also possible to arrange temperature sensors in the vicinity of the probes to make it possible to determine a relation between corrosive behaviour and temperature. The temperature sensors are preferably connected to recording equipment.

It is of course also possible to arrange such probes at diverse locations in the boiler lying further apart. More information is hereby also obtained concerning corrosivity of the flue gases at diverse locations and heights in the boiler.

What is claimed is:

1. Method for inspecting the quality of the corrosion on the inside of a wall of a water tube boiler manufactured from non-corrosion-resistant material of a space in which corrosive conditions prevail, comprising removing at least one part of the wall of the water tube boiler by means of non-destructive operations and subsequently subjecting the removed wall part to examination outside the space, wherein the part of the wall comprises a bolt having a shank having an end flush with the inside of the wall and wherein the end is exposed to the space.

2. Method as claimed in claim 1, further comprising replacing the part of the wall with a corresponding replacement part by non-machining operations.

3. Method as claimed in claim 1, further comprising examining the end exposed to the space.

4. Method as claimed in claim 3, further comprising comparing the part of the bolt exposed to the space with another part thereof.

5. Method as claimed in claim 1, further comprising sawing the removed part in the direction transversely of the plane of the wall and then inspecting the resulting sawn surface.

6. Method as claimed in claim 5, further comprising polishing the sawn surface prior to inspecting.

7. Method as claimed in claim 6, further comprising photographing the polished surface to form a photographic image.

8. Method as claimed in claim 7, further comprising converting the photographic image to digital form and quantifying the digital form.

9. A wall of a water tube boiler manufactured from non-corrosion resistant materials comprising a removable wall part attached to the wall for determining the quality of corrosion on the inside of the wall, wherein the wall encloses a space in which corrosive conditions prevail, wherein the wall is formed at least partially by water tubes, wherein the removable wall part is removable from the wall without destructive operations to allow the wall to be inspected outside the space, wherein the removable wall part is formed by a bolt screwed into an opening in the wall, wherein the opening is between two water tubes and the bolt is screwed into the opening up to a position in which the end of the bolt exposed to the space lies flush with the inner side of the wall, wherein the bolt comprises the same material as the wall and is coated with a layer of a precious metal at least at the end of the bolt exposed to the space.

10. The wall as claimed in claim 9, wherein the precious metal is gold or platinum.

11. The wall as claimed in claim 9, wherein the opening is provided with a helicoil.

\* \* \* \* \*

UNITED STATES PATENT AND TRADEMARK OFFICE
CERTIFICATE OF CORRECTION

PATENT NO. : 6,568,251 B1  Page 1 of 1
DATED : May 27, 2003
INVENTOR(S) : Walterus M. M. Huijbregts et al.

It is certified that error appears in the above-identified patent and that said Letters Patent is hereby corrected as shown below:

Column 4,
Line 28, "non-corrosion resistant" has been replaced with -- non-corrosion-resistant --.

Signed and Sealed this

Thirtieth Day of September, 2003

JAMES E. ROGAN
*Director of the United States Patent and Trademark Office*